United States Patent [19]

Insley et al.

[11] Patent Number: 4,711,848
[45] Date of Patent: Dec. 8, 1987

[54] SITE SPECIFIC MUTAGENESIS IN ALPHA-1-ANTITRYPSIN

[75] Inventors: Margaret Y. Insley, Woodinville; Glenn Kawasaki, Seattle, both of Wash.

[73] Assignee: ZymoGenetics, Inc., Seattle, Wash.

[21] Appl. No.: 709,382

[22] Filed: Mar. 7, 1985

Related U.S. Application Data

[63] Continuation-in-part of Ser. No. 589,410, Mar. 14, 1984, abandoned.

[51] Int. Cl.$^4$ .................. C12P 19/34; C12P 21/02; C12N 15/00; C12N 1/00
[52] U.S. Cl. .................................. 435/91; 435/70; 435/172.3; 435/317.1; 935/10; 935/8
[58] Field of Search ............... 435/68, 91, 172.3, 317, 435/70, 320; 935/6, 8, 9, 10, 11, 29

[56] References Cited

U.S. PATENT DOCUMENTS 4,351,901  9/1982  Bahl ................................. 435/68

FOREIGN PATENT DOCUMENTS 0114777  8/1984  European Pat. Off. ............. 935/8

OTHER PUBLICATIONS

Kurachi et al, "Cloning and Sequence of a cDNA Coding for Alpha Antitrypsin", Proceedings of the National Academy of Sciences 78(11), pp. 6826–6830 (1981).
Wallonne, Belgium Patent 895,961, Jun. 16, 1983, pp. 1–24, Chem. Abst. 99: 153208t.
Johnson et al, "Structural Evidence for Methionine at the Reactive Site of Human Alpha-1-Protease Inhibitor", Journal of Biological Chemistry 253, pp. 7142–7144 (1978).
Carrell et al, "Structure and Variation of Human Alpha Antitrypsin", Nature 298, pp. 329–334 (1982).
Rosenberg et al., "Synthesis in Yeast of a Functional Oxidation-Resistant Mutant of Human Alpha Antitrypsin" Nature 312, pp. 77–80 (1984).
Owen et al., "Mutation of Antitrypsin to Antithrombin" New England Journal of Medicine 309(12), pp. 694–698 (1983).
Stevens, et al., "Structure–Function Relationships in Lima Bean Protease Inhibitor", Bayer Symposium V, Proteinase Inhibitors, pp. 344–354 (1974) (Springer-Verlag).
Inouye, et al., "Role of Positive Charge on the Amino–Terminal Region of the Signal Peptide in Protein Secretion Across the Membrane", Proc. Natl. Acad. Sci. USA, vol. 79, pp. 3438–3441 (Jun. 1982).
Stone, et al., "Functional $\alpha_1$–Protease Inhibitor in the Lower Respiratory Tract of Cigarette Smokers", Science 221, pp. 1187–1189 (1983).
McRae, et al., "Studies on Reactivity of Human Leukocyte Elastase", Amer. Chem. Soc. (1980) pp. 3973–3978.
Dalbadie-McFarland, et al., "Oligonucleotide–directed mutagenesis as a general and powerful method for studies of protein function", Proc. Natl. Acad. Sci. USA vol. 79, pp. 6409–6413 (1982).
Winter, et al., "Redesigning Enzyme Structure by Site–Directed Mutagenesis", Nature, vol. 299, pp. 756–758 (1982).
Villafranca, et al., "Directed Mutagenesis of Dihydrofolate Reductase", Science, vol. 222, pp. 782–788 (1984).
Robey, et al., "Site-specific Mutagenesis of Aspartate Transcarbamoylase", J. of Biolog. Chem., vol. 259, No. 18, pp. 11180–11183 (1984).
Eisenbeis, et al., "Altered Cro Repressors From Engineered Mutagenesis of a Synthetic Cro Gene", Proc. Natl. Acad. Sci. USA, vol. 82, pp. 1084–1088 (1985).
Carter, et al., "The Use of Double Mutants to Detect Structural Changes in the Active Site of the Tyrosyl-tRNA Synthetase (Bacillus stearothermophilus)", Cell, vol. 38, pp. 835–840 (1984).

Primary Examiner—John Edward Tarcza
Attorney, Agent, or Firm—Flehr, Hohbach, Test, Albritton & Herbert

[57] ABSTRACT

Methods are provided for producing sites specific mutagenized alpha-1-antitrypsin. Particular mutants are formed having a mutation in the active site of alpha-1-antitrypsin at amino acid position 358 and at amino acid position 342.

17 Claims, 4 Drawing Figures

FIG. 1A

```
                                                          220                         230                         240
Asp Gln Val Thr Thr Val Lys Val Pro Met Lys Arg Leu Gly Met Phe Asn Ile Gln His Cys Lys Lys Leu Ser Ser Trp Val Leu
GAC CAG GTG ACC ACC GTG AAG GTG CCT ATG AAG CGT TTA GGC ATG TTT AAC ATC CAG CAC TGT AAG AAG CTC TCC AGC TGG GTG CTG
750                 760                 770                 780                 790                 800                 810                 820                 830
                                          250                         260                                            270
Leu Met Lys Tyr Leu Gly Asn Ala Thr Ala Ile Phe Phe Leu Pro Asp Glu Gly Lys Leu Gln His Leu Glu Asn Glu Leu Thr His Asp
CTG ATG AAA TAC CTG GGC AAT GCC ACC GCC ATC TTC TTC CTG CCT GAT GAC GGG AAA CTA CAG CAC CTG GAA AAT GAA CTC ACC CAC GAT
840                 850                 860                 870                 880                 890                 900                 910                 920
                           280                         290                                            300
Ile Ile Thr Lys Phe Leu Glu Asn Glu Asp Arg Arg Ser Ala Ser Leu His Leu Pro Lys Leu Ser Ile Thr Gly Thr Tyr Asp Leu Lys
ATC ATC ACC AAG TTC CTG GAA AAT GAA GAC AGA AGG TCT GCC AGC TTA CAT TTA CCC AAA CTG TCC ATT ACT GGA ACC TAT GAT CTG AAG
930                 940                 950                 960                 970                 980                 990                 1000                1010
                         310                        320                                       330
Ser Val Leu Gly Gln Leu Gly Ile Thr Lys Val Phe Ser Asn Gly Ala Asp Leu Ser Gly Val Thr Glu Glu Ala Pro Leu Lys Leu Ser
AGC GTG CTG GGT CAA CTG GGT ATC ACT AAG GTC TTC AGC AAT GGG GCT GAC CTC TCC GGG GTC ACA GAG GAG GCA CCG CTG AAG CTC TCC
1020                1030                1040                1050                1060                1070                1080                1090                1100
                                                         Lys (Z allele variant)                                                                    (Active site)
                      340                    ↑                           350                         360
Lys Ala Val His Lys Ala Val Leu Thr Ile Asp Glu Lys Gly Thr Glu Ala Ala Gly Ala Met Phe Leu Glu Ala Ile Pro Met Ser Ile
AAG GCC GTG CAT AAG GCT GTG CTG ACC ATC GAC GAG AAG GGG ACT GAA GCT GCT GGG GCC ATG TTT TTA GAG GCC ATA CCC ATG TCT ATC
1110                1120                1130                1140                1150                1160                1170                1180                1190
                     370                        380                                           390
Pro Pro Glu Val Lys Phe Asn Lys Pro Phe Val Phe Leu Met Ile Glu Gln Asn Thr Lys Ser Pro Leu Phe Met Gly Lys Val Val Asn
CCC GAG GTC AAG TTC AAC AAA CCC TTT GTC TTA ATG ATT GAA CAA AAT ACC AAG TCT CCC CTC TTC ATG GGA AAA GTG GTG AAT
1200                1210                1220                1230                1240                1250                1260                1270                1280
       394  STOP
Pro Thr Gln Lys
CCC ACC CAA AAA TAA CTG CCT CAA CCC CTC GCT CTC CCC TCC ATC CCT GGC CCC CTC CCT GGA TGA CAT TAA AGA AGG GTT GAG CTG
1290                1300                1310                1320                1330                1340                1350                1360                1370

C AAAAAAAAAAAAA CCCCCCCCCCCCCCCCCCCCCCCCCCCC 3'
1380           1390           1400           1410           1420           1430
```

FIG. 1B

M13 VECTORS

FIG. 2

M13mp11/pUC13

| | 1 | 2 | 3 | 4 | | 1 | 2 | 3 | 4 | 5 | 6 | 7 | 8 | 9 | 10 | 11 | 12 | 13 | 14 | 15 | 16 | | 5 | 6 | 7 | 8 |
|---|---|---|---|---|---|---|---|---|---|---|---|---|---|---|---|---|---|---|---|---|---|---|---|---|---|---|
| | THR | MET | ILE | THR | | PRO | SER | LEU | GLY | CYS | ARG | SER | THR | LEU | GLU | ASP | PRO | ARG | ALA | SER | SER | | ASN | SER | LEU | ALA |
| ATG | ACC | ATG | ATT | ACG | CCA | AGC | TTG | GGC | TGC | AGG | TCG | ACT | CTA | GAG | GAT | CCC | CGG | GCG | AGC | TCG | AAT | TCA | CTG | GCC |
| | | | | | HindIII | | | PstI | | SalI | XbaI | | BamHI | | | SalI | | | | EcoRI | | | HaeIII |
| | | | | | | | | | | AccI,HincII | | | | | | SmaI XmaI | | | | | | | |

FIG.—3

SITE SPECIFIC MUTAGENESIS IN ALPHA-1-ANTITRYPSIN

This is a continuation-in-part of copending Ser. No. 589,410, filed Mar. 14, 1984.

The present invention is directed to the preparation of mutagenized genes and expression of structural proteins thereof in microorganisms. Specifically, the present invention is directed to the preparation of mutagenized human alpha-1-antitrypsin genes and expression of site-specific mutants of alpha-1-antitrypsin.

Alpha-1-antitrypsin (hereinafter AT) is a protease inhibitor, the principal function of which is to inhibit elastase, a broad spectrum protease. Lung tissue in mammals is particularly vulnerable to attack by elastase, therefore AT deficiency or inactivation may lead to loss of lung tissue and elasticity and subsequently to emphysema. Loss or reduction of AT activity may be a result of oxidation of AT due to environmental pollutants, including tobacco smoke. Deficiency of AT may result from one of several genetic disorders. See Gadek, James E., and R. D. Crystal, "Alpha-1-Antitrypsin Deficiency", *The Metabolic Basis of Inherited Disease*, Stanbury, J. B., et al., Ed. McGraw-Hill, New York (1982) pp. 1450–1467; and Carroll, et al., *Nature* 2988, 329–334 (1982). Owen et al. (*New Eng. J. Med.* 309: 694–698, 1983) describe a condition in which a patient produced a mutant form of alpha-1-antitrypsin having an arginine substituted for the methionine at amino acid position 358. As the result of a single mutation in the gene sequence (ATG to AGG), the alpha-1-antitrypsin had been converted from its normal function as an elastase inhibitor to that of a thrombin inhibitor. This functional alteration results from a 30 percent homology in structure between wild-type AT and antithrombin III (see also Carroll et al., ibid). These findings indicate that an altered form of AT could be clinically important for use in inhibiting blood clotting, as for example, in the treatment of disseminated intravascular coagulation.

It is desirable to prepare altered forms of wild-type human AT which may result in enhanced stability, such as resistance to oxidation at the active site of the protein. It would also be desirable to prepare an altered form of wild-type AT for administration to persons suffering from a genetic deficiency in AT whereby the altered form is more immunologically compatible with such persons. It would also be desirable to prepare an altered form of AT having increased antithrombin activity.

It is therefore an object of the present invention to provide methods for preparing site-specific mutagenesis of wild-type human AT.

It is the further object of the present invention to provide expression vectors comprising structural genes encoding for mutagenized AT.

It is the further object of the present invention to provide site-specific mutagenized AT proteins.

The present invention provides methods for producing single and double-stranded closed circular DNA coding for a structural gene for a site-specific mutagenized AT. Specifically, a method is provided for producing single or double-stranded closed circular DNA coding for a structural gene for human X$^{358}$-AT wherein X is alanine, valine, glycine, phenylalanine, arginine or lysine, comprising the steps of:

(a) preparing a circular single-stranded cDNA molecule comprising the coding sequence or the complement of a structural gene for wild-type AT;

(b) annealing to such single-stranded DNA (1) a linear oligonucleotide characterized as being complementary to a segment of such single-stranded DNA, the oligonucleotide comprising a mismatch, or mismatches, at the codon corresponding to the amino acid in position 358 of wild-type AT wherein the mismatch(es) comprise one of the codons for alanine, valine, glycine, phenylalanine, arginine or lysine; and (2) a primer, such as the universal primer for M13;

(c) enzymatically extending the oligonucleotide and primer;

(d) ligating the termini of the extended oligonucleotide and primer together to form a gapped circle double-stranded DNA molecule; and (e) transfecting the double-stranded gapped circular DNA molecule into *E. coli* to produce the closed circular DNA molecule containing the structural gene for human X$^{358}$-AT, and after screening with the mutant oligonucleotide as a probe for plaque hybridization, isolating the mutant DNA.

By a similar method a closed circular DNA molecule may be prepared comprising the structural gene of human lys$^{342}$-AT, also known as the Z-allele of AT. The methods according to the present invention may also be utilized to prepare AT mutagenized at both positions 342 and 358, as well as at other positions.

The present invention also provides DNA constructs and cloning vectors comprising structural genes for mutagenized AT, methods for expression of the mutagenized proteins, and substantially pure site-specific mutagenized AT.

Figure 1A:
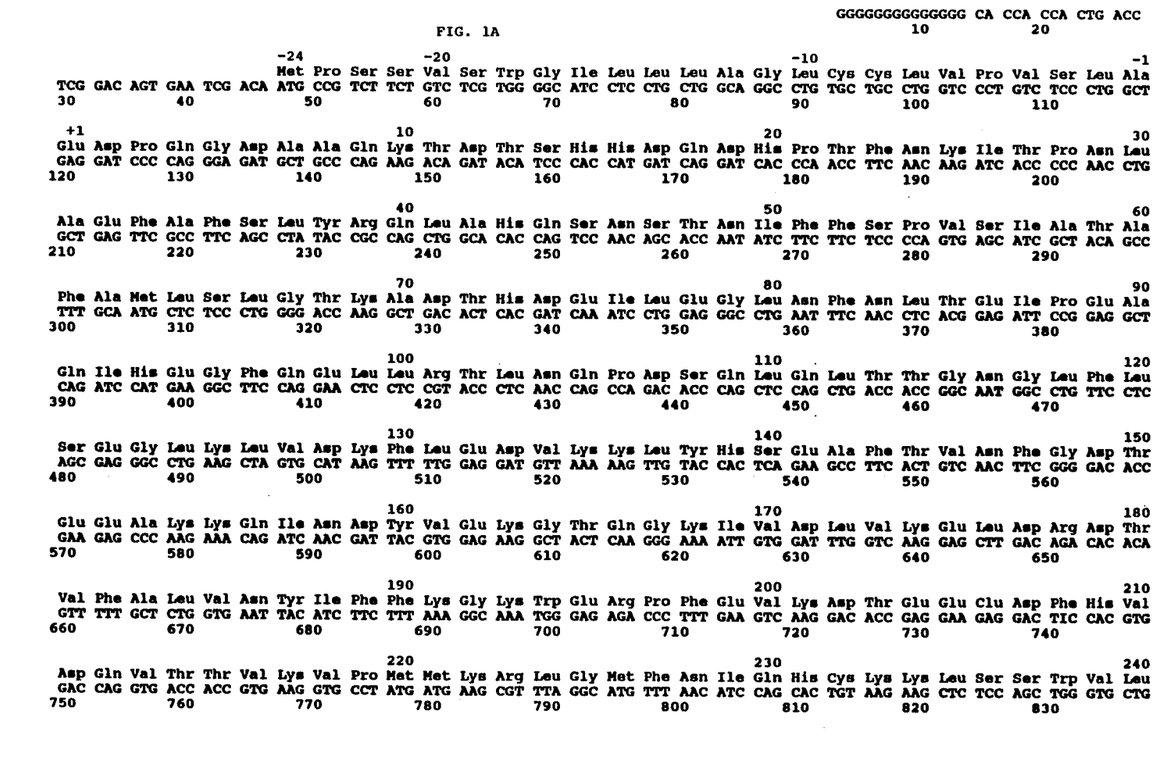
FIGS. 1A and 1B are the DNA and amino acid sequence for the structural gene and protein of the predominant form of human alpha-1-antitrypsin.
Figure 1B:
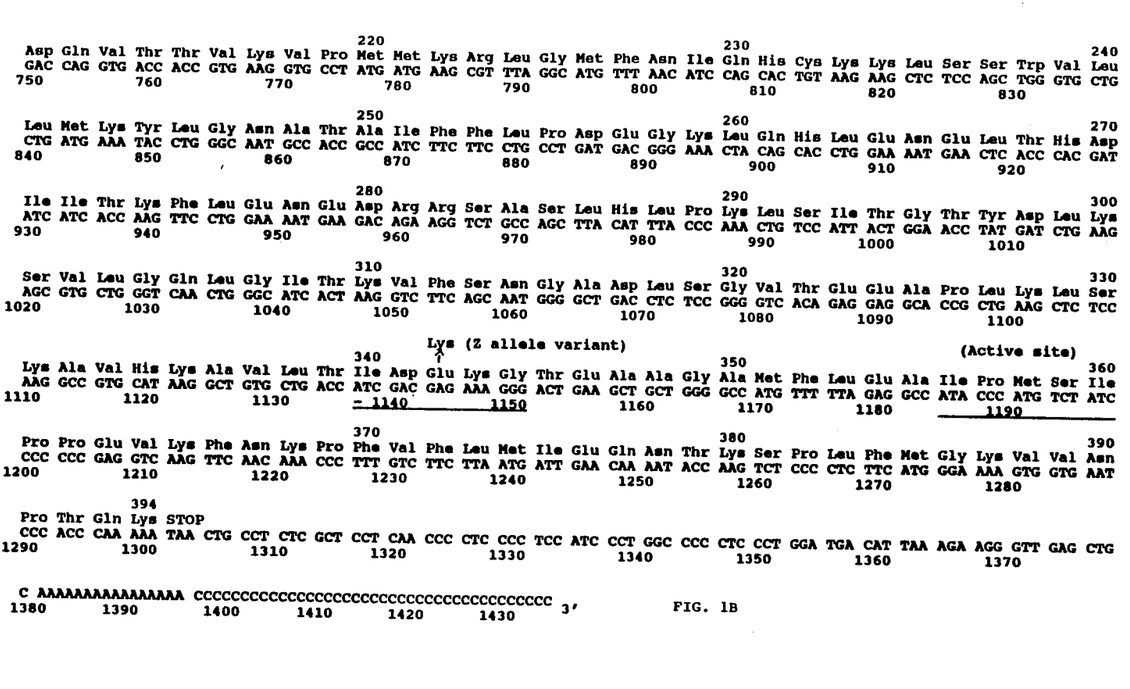

Referring to FIG. 1, there is shown the structural gene and amino acid sequence of the predominant form of wild-type AT. The active site of AT comprising the amino acids in positions 356 through 360 contains a methionine residue. The residue at position 358 may be subject to oxidation upon exposure to tobacco smoke or other oxidizing pollutants. Such oxidation may reduce the biological activity of AT, therefore substitution of another amino acid at that position, i.e. alanine, valine, glycine, phenylalanine, arginine or lysine, by site-specific mutagenesis may produce a form of AT which is more stable.

Furthermore, one of the genetic AT deficiencies is the formation of an abnormal form known as the Z-allele variant. Referring to FIG. 1, this mutation is manifested by the substitution of a lysine for a glutamic acid at amino acid position 342. Persons homozygous for the Z-allele variant produce approximately 15% of normal AT levels, apparently due to a block in processing in the liver. This results in the accumulation of an immature form of AT in the liver, with a corresponding decrease in plasma levels of the inhibitor. Up to 80% of persons having this condition can be expected to die of chronic lung and/or liver disease. It should be noted that the Z-allele variant protein itself has the same anti-elastase activity as the wild-type protein. The AT levels of such persons may be augmented by intravenous administration of wild-type AT. (See Gadek, et al., *Journal of*

*Clinical Investigation* 68, 1158–1165 (1981)). However, as the wild-type protein is foreign to these patients, some ZZ individuals may be expected to become allergic to it. Thus, the present invention provides for the method of producing the Z-allele variant, which may be non-immunogenic in certain AT deficient patients.

The arg[358]-AT, which has been shown to possess antithrombin activity, may also be useful for inhibiting blood clotting. Naturally occurring antithrombin III functions normally in the body to regulate blood coagulation. Antithrombin III has been used for the treatment of disseminated intravascular coagulation (Gassner, A. et al., *Wien Klin. Wochenschr.* 91: 51–53, 1979; and Hellgren, M. et al., *Gynecol. Obstet. Invest.* 16: 107–118, 1983), and as a substitute for heparin in the treatment of other conditions (Bernhardt, W., and Novakova-Banet, A., *Ric. Clin. Lab.* 13: 61–66, 1983).

Particularly, the present invention is directed to preparation of a single-stranded DNA template comprising cDNA of the wild-type human AT gene or a complement thereof. A linear oligonucleotide primer containing one or more mismatches at the codon which is to be mutated is annealed to the template, together with a second primer which anneals to the 5' side of the mutagenic site. A preferred second primer is the universal primer of M13 which is commercially available and hybridizes to the lac Z gene in M13 vectors (Messing, *Meth. in Enzymology* 101: 20–77, 1983. The oligonucleotides are extended and ligated at the termini to yield a double-stranded gapped circular DNA. This double-stranded DNA is utilized to transfect the host microorganism, *E. coli*, which will result in a population which contains a mixture of mutant and wild-type DNA molecules. The mutant DNA molecules are selected by plaque hybridization using the mutant DNA oligonucleotide as probe. The DNA may be sequenced to verify the presence of an altered codon and then cloned into appropriate expression vectors. The mutagenized AT protein may be expressed in bacteria, yeast, or other prokaryotes or eukaryotes.

As used herein, the terms "DNA construct," "vector," and "plasmid" constitute any DNA molecule which has been modified by human intervention, or which is a clone of a molecule which has been so modified, to contain segments of DNA which are combined and juxtaposed in a manner which would not otherwise exist in nature. The term "expression vector" as used herein will be a DNA construct which will contain genetic information which insures its own replication when transformed into a host organism, and at least one gene to be expressed in the host organism, as well as other control functions which may be necessary for expression to occur, such as a site for initiation of transcription, initiation of translation, a promoter region and, in some cases, a terminator region. The term "expression" is defined in its common usage to mean the condition wherein a protein product, coded by a gene present in the host organism, is synthesized by an organism. The term "gapped" refers to a DNA molecule which is substantially double-stranded but contains single-stranded regions.

MATERIALS AND METHODS

Standard biochemical techniques were utilized throughout. M13 host strains, universal primer and vectors were obtained from Bethesda Research Laboratories. Restriction endonucleases were obtained from Bethesda Research Laboratories, New England BioLabs, and Boehringer Mannheim Biochemicals, and used according to the manufacturers' directions. General cloning procedures, including transformation of bacterial cells, a method for the blunting of DNA fragments using DNA polymerase I (Klenow fragment) and the joining of DNA fragments using T4 DNA ligase are described by Maniatis et al. (*Molecular Cloning: A Laboratory Manual*, Cold Spring Harbor Laboratory, 1982.)

A general method for site-specific mutagenesis is described by Zoller, Mark J. and M. Smith, "Oligonucleotide-Directed Mutagenesis of DNA Fragments Cloned Into M13 Derived Vectors", *Manual for Advanced Techniques in Molecular Cloning Course*, Cold Spring Harbor Laboratory, 1983.

Oligonucleotides which contain one or more base alterations from sequences in wild-type AT may be prepared by the phosphite-triester method, generally disclosed in Beaucage and Caruthers, *Tetrahedron Letters* 22: 1859–1862, 1981, and Matteucci and Caruthers, *J. Am. Chem. Soc.* 103: 3138 (1981), using a polymer support as described in Matteucci and Caruthers, *Tetrahedron Letters* 21: 719–722 (1980). Alternatively, the oligonucleotides may be synthesized by machine, such as an Applied Biosystems Model 380-A DNA synthesizer. Synthesized oligonucleotides may be purified by polyacrylamide gel electrophoresis on denaturing gels. The oligonucleotides may be phosphorylated at the 5'-end by (gamma) $^{32}$P-ATP and polynucleotide kinase. Verification of the oligonucleotide sequences may be performed by the Maxam and Gilbert procedure, *Methods in Enzymology*, 65: 57 (1980).

PREPARATION OF SINGLE STRANDED DNA COMPRISING WILD-TYPE ALPHA-1-ANTITRYPSIN GENE

Figure 2:
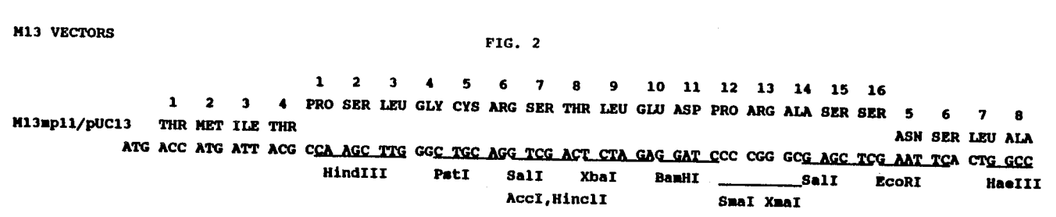
FIG. 2 is the DNA sequence of pUC13 comprising the multiple restriction site at the start of the lacZ gene.

The gene coding for the predominant form of human AT (FIG. 1) may be isolated from a human liver cDNA library by conventional procedures using the baboon sequence (Kurachi et al, *Proc. Nat. Acad. Sci. USA*, 78, 6826–6830 (1980)); and Chandra et al, *Biochem. Biophys. Res. Com.*, 103, 751–758 (1981) as a DNA hybridization probe. The AT gene is isolated as a 1446 bp Pst1 fragment and inserted into Pst1 digested plasmid pUC13 (prepared as described by Vieira et al, *Gene*, 19, 259–268 (1982) for vectors pUC8 and pUC9, but containing the multiple restriction site shown in FIG. 2 at the start at the lacZ gene) to give recombinant plasmid pUCα1 which contains the BamH1 site in the polylinker on the 3' side of the AT gene. The plasmid pUCα1 is digested with BamH1 to obtain the AT sequence. The 1320 bp BamH1 fragment may then be ligated into M13 mp10 (Messing, *Methods in Enzymology* 101: 20–77 (1983)) and the resultant recombinant phage used to transfect *E. coli* K12 (JM103). The single-stranded closed circular DNA containing the AT gene is then isolated by the procedure of Zoller and Smith, ibid.

PREPARATION OF OLIGONUCLEOTIDES CONTAINING ONE OR MORE BASE ALTERATIONS FROM SEQUENCES IN WILD-TYPE AT

Oligonucleotides shown below in TABLE 1 may be synthesized by the conventional phosphite-triester method or on an Applied Biosystems Model 380-A synthesizer, followed by purification on denaturing polyacrylamide gels. The oligonucleotides code for amino acids 356 through 360 of wild-type human AT shown in FIG. 1 except that appropriate mismatches for the codon for amino acid 358 are present.

TABLE 1

Active Site Mutagenesis

| Amino Acid 358 | Oligonucleotide for nucleotides 1184–1198 |
| --- | --- |
| Methionine (wild-type) | ATACCC<u>A</u><u>T</u><u>G</u>TCTATC |
| Alanine | ATACCC<u>GC</u>GTCTATC |
| Valine | ATACCC<u>GT</u>GTCTATC |
| Glycine | ATACCC<u>GGG</u>TCTATC |
| Phenylalanine | ATACCC<u>TTC</u>TCTATC |
| Arginine | ATACCC<u>AGA</u>TCTATC |
| | ATACCC<u>AGG</u>TCTATCCCC |
| Lysine | ATACCC<u>AAG</u>TCTATC |

It will be appreciated that oligonucleotides longer than those above may be used. It will also be appreciated that other mutant codons could be substituted for those shown, due to the degeneracy of the genetic code. It is preferred that the oligonucleotides be in the range of 15–21 nucleotides in length and include at least nucleotides 1184–1198.

Another oligonucleotide is prepared as shown in TABLE 2 which corresponds to a sequence approximately centered about the codon for amino acid 342 in the AT sequence. The oligonucleotide in TABLE 2 contains a mismatch at the codon for amino acid 342 whereby the codon for lysine is included to produce the Z-allele variant.

TABLE 2

Z-Allele Variant Site Mutagenesis

| Amino Acid 342 Mutation | Oligonucleotide for Nucleotides 1135–1149 |
| --- | --- |
| Lysine | CATCGACAAGAAAGG |

It will be appreciated that longer oligonucleotides may be utilized. It will also be appreciated that other mutant codons could be substituted for those shown, due to the degeneracy of the genetic code. It is preferred that the oligonucleotides be in the range of 15–21 nucleotides in length and contain nucleotides 1135–1149.

EXTENSION AND LIGATION OF OLIGONUCLEOTIDES

Each of the above-identified oligonucleotides, together with a second primer, such as the universal primer of M13, is annealed to the single-stranded recombinant M13 phage DNA containing the wild-type AT gene. In a typical procedure 20 pmol of phosphorylated Z-allele oligonucleotide and 20 pmol of M13 primer were mixed with 1 pmol of the recombinant M13 phage containing the AT cDNA and allowed to anneal. The oligonucleotides were then extended using DNA polymerase I (Klenow fragment) and the ends of the synthesized strands were joined, using T4 DNA ligase. The resulting DNA molecules are significantly double-stranded over the AT coding region and partially single-stranded over the M13 vector region. These gapped DNA circles may be transfected into competent E. coli K12 (JM101) where the gaps are filled by the bacterial DNA repair system to make active phage. A population of mutant molecules are distinguished from wild-type by the plaque-lift hybridization method (Zoller et al., ibid) wherein phage DNA is bound to a nitrocellulose filter and probed with $^{32}$P-labelled mutagenic oligonucleotide. The principle behind this procedure is that the mutagenic oligonucleotide will form a more stable duplex with a mutant clone than with a wild-type clone (hybridization with a wild-type clone results in a mismatch). Following hybridization at low temperature, the wash temperature is increased until only the mutant molecules hybridize with the probe. Typically, hybridization may be performed at a temperature of 23° C., followed by successive washes at 23°, 37°, 50°, and 55°, with autoradiography following each wash. The mutant phage may be then isolated, replated, and the presence of the mutation verified by sequencing using the dideoxy method of Sanger et al. (J. Mol. Biol. 143: 161, 1983) and Sanger et al. (Proc. Nat. Acad. Sci. USA 74: 5463, 1977).

CLONING OF MUTANT AT SEQUENCES INTO BACTERIAL EXPRESSION VECTORS

The mutant AT coding regions may be removed from the closed circular DNA by digestion of the replicative form with BamH1 and Pst1. The fragments containing the mutant AT gene may be inserted into BamH1 and Pst1 digested vectors M13 TAC or M13 mp10. The phage M13 mp10 is commercially available from P-L Biochemicals or Bethesda Research Laboratories. The resulting constructs may be used to transform E. coli K12 (JM103) as described above.

M13TAC is prepared by digesting the phage M13 mp10 with EcoRI and BamH1. A synthetic DNA adaptor, purchased from P-L Biochemicals, having the following structure and lacking the five prime phosphates is ligated onto the resultant sticky ends to form the construct mp10A. The construct mp10A thus contains EcoRI and BamH1 restriction sites about a sequence including ATGGAG which provides the initiation codon and the first amino acid (Glu) codon for the AT gene. The substitution of the adaptor for the region between the original EcoRI and BamH1 sites of mp10 destroys the lac operon reading frame and the resulting transfectants give white plaques.

The vector mp10A is digested with AvaII and the sticky ends filled using the Klenow fragment of DNA polymerase. This is followed by digestion with EcoRI, and removal of the sticky end using S1 nuclease. The resultant blunt end fragment is mp10B.

A DNA fragment comprising the trp-lac promoter is removed from pDR540, a commercially available plasmid (P-L Biochemicals). The plasmid pDR540 is cut with HindIII and the sticky ends are filled with Klenow polymerase. Linkers having the sequence CCTCGAGG are ligated to the blunt ends and excess linkers are removed by digestion with XhoI. The resulting construct, known as pDR540X, contains an XhoI site in place of the HindIII site of pDR540. Digesting pDR540X with XhoI and BamH1, following by blunting the ends using Klenow fragment, yields a fragment containing the trp-lac promoter (TAC) and Shine-Dalgarno sequence. The above described fragment containing the trp-lac promoter is inserted into the mp10B fragment producing the hybrid phage mp10C. Ligation of the blunted AvaII end of mp10B to the blunted XhoI end of the TAC containing fragment regenerates an XhoI site at the junction. Ligation of the blunted BamH1 site of the TAC fragment to the blunted EcoRI end of mp10B creates an NcoI site (CCATGG) at this junction. The proper orientation of the fragment may be screened for by the formation of blue plaques. The phage mp10C contains a second BamH1 site located upstream of the ATG initiation codon which must be removed to facilitate insertion of the AT gene into the original BamH1 site. To remove this extraneous BamH1 site, mp10C is subjected to two digestions with BamH1. The first, a partial digestion, is followed by filling in the sticky ends with Klenow polymerase, digesting with XhoI, and purifying on an agarose gel. The proper fragment is identified as the one containing the NcoI restriction site. The second BamH1 digestion of mp10C is run to completion, the sticky ends are filled using Klenow polymerase and $\alpha$-$^{32}$P-dNTP's are used to facilitate monitoring of subsequent manicuring of the blunt ends by Bal 31 exonuclease. Five base pairs are removed from the labeled terminus by Bal 31 exonuclease, thereby eliminating the BamH1 site. The sequence containing the promoter is removed with XhoI and gel purified. The mp10 and pDR540-derived fragments are ligated together, cloned into *E. coli* K12 (JM103) (Messing, J. et al. 1981 *Nucleic Acids Res.* 9: 309, commercially available from P-L Biochemicals) and screened for NcoI sensitivity and formation of blue plaques. The resulting vector, is M13 TAC.

CLONING OF EXPRESSION VECTORS IN YEAST

For cloning and expression in yeast, the mutant AT sequences may be isolated from the replicative forms of the M13 phage containing the mutant sequences as BamH1 fragments and inserted into BamH1 digested plasmid HAT4. Plasmid HAT4 was constructed in the following manner. Plasmid pJDB248 (Beggs, *Nature* 275: 104–109, 1978) was partially digested with EcoRI and the pMB9 sequence was removed. Plasmid pBR322 (Bolivar et al. *Gene* 2: 95–113, 1977) was cleaved with EcoRI and joined to the linearized pJDB248 in place of the pMB9 sequence. The resultant plasmid is known as C1/1. The yeast TPI promoter was removed from plasmid pTPIC10 (Alber and Kawasaki, *J. Mol. Appl. Genet.* 1: 419–434, 1982) by partial Bgl II digestion, religation, and digestion with Kpn I. Approximately 50 μg of the resulting linearized plasmid was treated with 5 units of Bal 31 for five minutes at 30° C. The DNA was then treated with DNA polymerase I (Klenow fragment) to blunt the ends of the molecule. Hind III linkers (CAAGCTTG) were then added. A plasmid was identified which contained the Hind III linker at position +4 of the TPI coding region. This plasmid was cut with Hind III, digested for a few seconds with Bal 31, and blunted with DNA polymerase I (Klenow fragment). EcoRI linkers (GGAATTCC) were then added, and the DNA was digested with Bgl II and EcoRI, and the fragment comprising the TPI promoter was isolated. This fragment was inserted into YRp7' (Stinchcomb et al., *Nature* 282: 39–43, 1979) which had been linearized with Bgl II and EcoRI. One such plasmid, designated TE32, contained the EcoRI linker at approximate position −14 in the TPI sequence. TE32 was cut with EcoRI and BamH1, and ligated with a 10-fold excess of a linker having the sequence:

AATTCATGGAG
GTACCTCCTAG.

The resultant plasmid was cut with BamH1 and religated to produce plasmid TEA32. The TPI promoter fragment was then removed from TEA32 as a Bgl II-BamH1 fragment of about 900 base pairs, and inserted into the BamH1 site of C1/1. Plasmid pUCα1 was then cleaved with Xba I and EcoRI and the yeast TPI terminator, obtained from plasmid pTPIC10 (Alber and Kawasaki, ibid) as a 700 base pair Xba I-EcoRI fragment, was inserted downstream of the AT sequence. An EcoRI-BamH1 synthetic DNA adapter was then added at the EcoRI site. The resultant plasmid was then digested with BamH1 to liberate a fragment of approximately 2100 base pairs comprising the AT coding sequence and the TPI terminator. This fragment was inserted into the BamH1 site of the plasmid comprising C1/1 and the TPI promoter. The resultant plasmid was designated HAT4. The resulting expression vector may be used to transform yeast strains to express the mutagenized protein. Preferred yeast strain hosts are GK100, ATCC No. 20669; and *S. cerevisiae* strain E2-7B, ATCC No. 20689.

Additionally, the mutant sequences may be inserted into other yeast expression vectors, for example YEp13 (Broach et al., *Gene* 8: 121: 133, 1979), YRp7 Struhl et al., *Proc Nat. Acad. Sci USA* 76: 1035–1039, 1979), C1/1 (described above), other plasmids containing 2μ or ARS sequences, and derivatives thereof.

Alternatively, expression may be achieved by integration of said AT mutant sequences into the host chromosome. In this instance, the AT sequences will be linked, in proper orientation, to appropriate transcription promoter and terminator sequences.

EXPRESSION OF $X^{358}$-AT IN YEAST

Expression Of val$^{358}$-AT In Yeast

Figure 3:
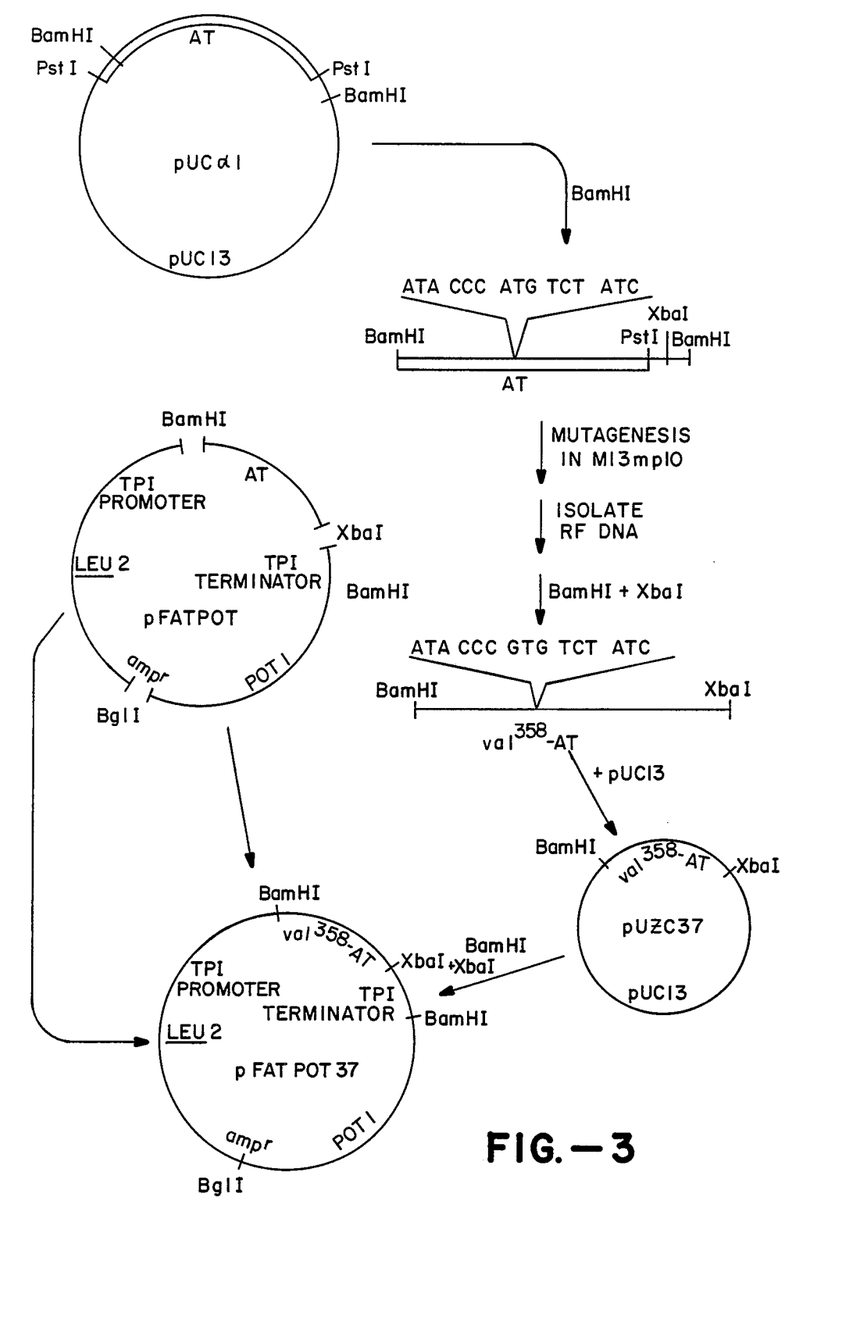
FIG. 3 is a scheme for preparing vector pFATPOT37 containing the mutant val$^{358}$-AT sequence.

A preferred vector for expression of mutant AT genes in yeast is the C1/1 derivative pFATPOT (FIG. 3; *S. cerevisiae* strain E18 transformed with pFATPOT has been deposited with ATCC under accession No. 20699. pFATPOT is available by extraction from lysed cells of this transformant.). The vector pFATPOT comprises the amp$^r$, LEU2, and 2μ regions of C1/1; an expression unit consisting of the *S. cerevisiae* triose phosphate isomerase (TPI) promoter, the wild-type AT sequence from pUCα1, and the *S. cerevisiae* TPI transcription terminator; and the *Schizosaccharomyces pombe* triose phosphate isomerase (POT1) gene. When transformed into a yeast host defective in triose phosphate isomerase production, the POT1 gene on the plasmid complements the host cell defect and allows for plasmid maintenance at high copy number during growth on rich media.

Referring to FIG. 3, pUCα1 was cleaved with BAM HI, and the ca. 1400 bp fragment comprising the AT sequence was gel purified. This fragment was then ligated to BamH1 digested M13mp10 (replicative form) in the proper orientation to allow hybridization of the single-stranded phage with the oligonucleotides of Table 1. The AT sequence was then mutagenized as described above to produce the sequence encoding val$^{358}$-AT. The mutagenized sequence was then removed from the M13 vector by digestion of replicative form DNA with Bam HI and Xba I. The mutant AT sequence was inserted into pUC13 which has been linearized by digestion with Bam HI and Xba I. The resulting recombinant plasmid was designated pUZC37.

Again referring to FIG. 3, a yeast expression vector for val$^{358}$-AT was constructed in the following manner. The mutant AT sequence was purified from pUZC37 by digestion with Bam HI and Xba I. The fragment comprising the TPI promoter and upstream portion of the amp$^r$ gene was removed from pFATPOT by digestion with Bam HI and Bgl I and was gel purified. pFATPOT was also digested with Xba I and Bgl I and the fragment comprising the TPI terminator and the downstream portion of the amp$^r$ gene was purified. The three fragments were ligated together and used to transform E. coli RRI (ATCC 31343). Transformants were screened for ampicillin resistance. The resultant plasmid was designated pFATPOT37.

S. cerevisiae strain E18 (deposited with American Type Culture Collection, accession no. 20743) was transformed with pFATPOT37, grown to stationary phase overnight in Medium I (6% glucose, 2% Yeast Extract, 0.5% Ammonium Sulfate) and assayed for production of elastase inhibiting activity and trypsin inhibiting activity as described below, using human α-1 antitrypsin (Sigma Chemical Co.) and met$^{358}$-AT produced in yeast transformed with pFATPOT as assay standards. Yeast samples were prepared for assay by grinding the cells with glass beads in phosphate buffered saline.

Expression Of arg$^{358}$-AT In Yeast

A yeast expression vector for arg$^{358}$-AT was constructed as described for pFATPOT37, but using the oligonucleotide ATA CCC AGG TCT ATC CCC in the mutagenesis step. The final expression vector was designated pFATPOT136. S. cerevisiae strain E18 was transformed with pFATPOT136, and was grown and assayed as described below. Results are given in TABLE 3.

ELASTASE INHIBITION ASSAY

To a 200 μl sample containing AT, 10 μl of 1 μg/μl porcine pancreatic elastase (Sigma) in 0.2M Tris pH 8.8 was added. Phosphate buffered saline was added to a total volume of 1 ml and the mixture was incubated 15 minutes at 4° C. 1 ml of 10 mg/ml elastin-orcein (Sigma) in 0.4M Tris pH 8.8 was then added and the mixture incubated 60 minutes at 37° C. with mixing at 15-minute intervals. The mixture was centrifuged and the $A_{590}$ of the supernatant was measured. The results of the assay on human AT and on met$^{358}$-AT, val$^{358}$-AT and arg$^{358}$-AT, prepared as described above, are shown in TABLE 3.

TRYPSIN INHIBITION ASSAY

To a 50 μl sample containing AT, 40 μl of 6 μg/ml trypsin (from bovine pancrease, Sigma) in 2.5 mM HCl was added. The volume was adjusted to 500 μl with 0.1M Tris, 0.02M CaCl$_2$ pH 8.2 and the mixture was incubated 10 minutes at room temperature. One ml of 10 mg/ml Azocoll (Calbiochem) in phosphate buffered saline was added and the mixture was incubated 30 minutes at 37° C. with mixing at 10-minute intervals. The mixture was centrifuged and the $A_{520}$ of the supernatant was measured. The results of the assay on human AT and on met$^{358}$-AT, val$^{358}$-AT and arg$^{358}$-AT, prepared as described above, are shown in TABLE 3.

TABLE 3

| | Concentration (μg/ml) | Elastase Inhibition ($A_{590}$) | Trypsin Inhibition ($A_{520}$) |
|---|---|---|---|
| Human AT | 200 | .166 | .030 |
| | 100 | .372 | .071 |
| | 10 | .482 | .172 |
| | 1 | .502 | .247 |
| | 0.1 | .460 | .219 |
| Met$^{358}$—AT (Yeast) | 200 | .207 | .045 |
| | 100 | .344 | .060 |
| | 10 | .499 | .199 |
| | 1 | .498 | .235 |
| | 0.1 | .497 | .240 |
| val$^{358}$-AT (Yeast) | 200 | .175 | .120 |
| | 100 | .202 | .168 |
| | 10 | .494 | .167 |
| | 1 | .487 | .166 |
| | 0.1 | .477 | .194 |
| arg$^{358}$-AT (Yeast) | 200 | .480 | .027 |
| | 100 | .488 | .019 |
| | 10 | .499 | .124 |
| | 1 | .463 | .166 |
| | 0.1 | .471 | .191 |
| Control (no AT) | — | .500 | .138 |
| Human AT, 200 μg/ml without trypsin | — | — | .032 |

The mutagenized proteins according to the present invention may be purified from extracts of the transformed yeast cells by immuno adsorption. An immuno adsorption column may be prepared by covalently attaching affinity-purified antibodies to alpha-1-antitrypsin to CNBr-activated Sepharose according to the method of Cuatrecasas (J. Biol. Cheml. 245: 3059, 1970). Disrupted cells are extracted with three volumes of phosphate buffered saline pH 7.2 containing 0.5M NaCl and the extract is applied to the column. The column is eluted with 3M NaSCN.

The site specific mutagenized AT proteins according to the present invention may be useful in treatment of genetic antitrypsin deficiency, such as found in genetic ZZ-individuals, and other disease states related to inadequate levels of AT or to conditions whereby the patient displays antigenic reactions to wild-type AT. Thus, conditions such as emphysema and other lung disorders related to progressive digestion of lung sacs may be treated, such as chronic obstructive pulmonary disease or adult respiratory distress syndrome. Non-genetically related emphysema may also be treated such as emphysema resulting from heavy smoking. Conditions not necessarily confined to the lungs may also be treated such as cystic fibrosis and arthritis. For a review of alpha-1-antitrypsin, see Gadek, ibid.

In addition to the above-described uses of the mutant forms of AT, the protein comprising the methionine to arginine mutation at amino acid 358 may be used for inhibition of blood clotting, for example, in treating disseminated intravascular coagulation.

The proteins in accordance to the present invention may be admixed with conventional pharmaceutical carriers. Preferably the proteins may be administered intravenously or by inhalation. While effective dosages may vary according to the severity of the condition and weight of the subject, dosages in the range of 0.5 to 10.0 grams per week of a protein introduced intravenously may, in many cases, be effective. Lower dosages may be effective if the method of administration is by inhalation. Oral administration may also be effective provided the site specific mutagenized AT is protected in capsules or coated carriers to prevent premature degradation in the digestive tract.

Having described a specific preferred embodiments of the present invention, other modifications and other embodiments may be apparent to those ordinarily skilled in the art. Such modifications and embodiments are intended to be within the scope of the present invention.

What is claimed:

1. A method for producing closed circular DNA molecules coding for a human structural gene for $X^{358}$-alpha-1-antitrypsin wherein X is alanine, valine, glycine, phenylalanine, arginine or lysine, comprising the steps of:
   (A) preparing a circular single-stranded cDNA molecule comprising the coding sequence or the complement of the structural gene for wild-type human alpha-1-antitrypsin;
   (B) annealing to said single-stranded cDNA (1) a linear oligonucleotide, characterized as being complementary to a segment of said single-stranded DNA, and comprising a codon mismatch corresponding to the amino acid in position 358 of said wild-type alpha-1-antitrypsin, wherein said mismatch comprises a codon for alanine, valine, glycine, phenylalanine, arginine or lysine; and (2) a primer;
   (C) extending said oligonucleotide and primer;
   (D) ligating the termini of said extended oligonucleotide and primer to form a gapped circular double-stranded DNA molecule;
   (E) transfecting said double-stranded gapped circular DNA into a host microorganism to form said closed circular DNA molecule comprising said structural gene coding for human $X^{358}$-alpha-1-antitrypsin.

2. A method according to claim 1 further comprising steps of (F) cloning said structural gene from step (E) into an expression vector and (G) expressing human $X^{358}$-alpha-1-antitrypsin in a microorganism.

3. A method according to claim 2 wherein said microorganism is a bacterium.

4. A method according to claim 2 wherein said microorganism is yeast.

5. A method for expression of a mutant form of human alpha-1-antitrypsin comprising the step of transforming a host microorganism with a DNA construct comprising a structural gene containing at least one mutated codon, said gene coding for a mutant form of human alpha-1-antitrypsin, wherein said mutated codon is codon 358 which results in an amino acid substitution in position 358 of human alpha-1-antitrypsin, and said construct being capable of replication in said host microorganism.

6. A method according to claim 5 wherein said microorganism is a bacterium.

7. A method according to claim 5 wherein said microorganism is a fungus.

8. A method according to claim 5 wherein said microorganism is a yeast.

9. A method according to claim 5 wherein said mutated codon is codon 358 and said mutant form is $arg^{358}$-alpha-1-antitrypsin.

10. A method according to claim 5 wherein said mutated codon is codon 358 and said mutant is $val^{358}$-alpha-1-antitrypsin.

11. A DNA construct comprising a structural gene containing at least one mutated codon, said gene coding for a mutant form of human alpha-1-antitrypsin wherein said mutated codon is codon 358 which results in an amino acid substitution in position 358 of human alpha-1-antitrypsin.

12. A DNA construct according to claim 11 which results in alanine at position 358.

13. A DNA construct according to claim 11 which results in valine at position 358.

14. A DNA construct according to claim 11 which results in glycine at position 358.

15. A DNA construct according to claim 11 which results in phenylalanine at position 358.

16. A DNA construct according to claim 11 which results in arginine at position 358.

17. A DNA construct according to claim 11 which results in lysine at position 358.

* * * * *

UNITED STATES PATENT AND TRADEMARK OFFICE
CERTIFICATE OF CORRECTION

PATENT NO. : 4,711,848

DATED : December 8, 1987

INVENTOR(S) : Margaret Y. Insley et al.

It is certified that error appears in the above—identified patent and that said Letters Patent is hereby corrected as shown below:

In the Abstract, in the first line, delete "sites specific" and insert --site-specific-- therefor.

In column 1, in line 26, delete "Carroll" and insert --Carrell-- therefor; delete "2988" and insert --298-- therefor.

In column 3, in line 28, delete "1983" and insert --1983)--.

In column 4, in line 41, delete "(1980))" and insert --(1980)-- therefor;
in line 42, delete "(1981)" and insert --(1981))-- therefor.
in line 47, delete "at" (second instance) and insert --of-- therefor.

In column 6, in line 1, delete "are" and insert --is-- therefor.

In column 7, in line 32, delete ",".

In column 10, in line 36, delete "Chem1" and insert --Chem.-- therefor.

UNITED STATES PATENT AND TRADEMARK OFFICE
CERTIFICATE OF CORRECTION

PATENT NO. : 4,711,848

DATED : December 8, 1987

INVENTOR(S) : Margaret Y. Insley  et al.

It is certified that error appears in the above-identified patent and that said Letters Patent is hereby corrected as shown below:

Column 1, in the first line of text, delete "copending";
in line 2, after "1984.", insert -- abandoned --.

Signed and Sealed this

Thirty-first Day of January, 1989

Attest:

DONALD J. QUIGG

*Attesting Officer*   *Commissioner of Patents and Trademarks*